United States Patent
Hein et al.

(10) Patent No.: US 7,191,093 B2
(45) Date of Patent: Mar. 13, 2007

(54) COMPUTER TOMOGRAPHY UNIT WITH A DATA RECORDING SYSTEM

(75) Inventors: Peter Hein, Bamberg (DE); Jürgen Simon, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/516,829

(22) PCT Filed: May 23, 2003

(86) PCT No.: PCT/DE03/01666

§ 371 (c)(1),
(2), (4) Date: Dec. 7, 2004

(87) PCT Pub. No.: WO03/103494

PCT Pub. Date: Dec. 18, 2003

(65) Prior Publication Data

US 2005/0246120 A1    Nov. 3, 2005

(30) Foreign Application Priority Data

Jun. 7, 2002   (DE) ................................ 102 25 613

(51) Int. Cl.
*G06F 11/30* (2006.01)
(52) U.S. Cl. .................................................... 702/182
(58) Field of Classification Search ................. 702/182
See application file for complete search history.

(56) References Cited

U.S. PATENT DOCUMENTS

| | | | |
|---|---|---|---|
| 5,220,589 A * | 6/1993 | Gard ........................... 378/19 |
| 5,600,574 A | 2/1997 | Reitan | |
| 5,786,994 A * | 7/1998 | Friz et al. ..................... 700/79 |
| 6,264,365 B1 | 7/2001 | Patch | |
| 6,275,559 B1 | 8/2001 | Ramani et al. | |
| 6,327,330 B1 | 12/2001 | Peter | |
| 6,424,159 B1 | 7/2002 | Jansen et al. | |
| 6,505,966 B1 * | 1/2003 | Guru ........................... 378/207 |

FOREIGN PATENT DOCUMENTS

| | | |
|---|---|---|
| DE | 100 49 405 A1 | 5/2001 |
| DE | 101 20 088 A1 | 10/2001 |

* cited by examiner

*Primary Examiner*—John Barlow
*Assistant Examiner*—Jonathan Moffat
(74) *Attorney, Agent, or Firm*—Harness, Dickey & Pierce, P.L.C.

(57) ABSTRACT

A computed tomography unit includes a radiation detector with several detector elements, a data recording system for reading the electrical signals generated by the detector elements and the processing thereof to give raw data may be supplied via a data transmission path. The computed tomography unit further includes an analytical device for the automatic determination of the quality of the data recording system and/or of the data transmission path and optionally the radiation detector in addition. The analytical unit in particular initiates a measurement for the generation of raw data, calculates at least one value for at least one parameter which permits a quality determination therefrom and displays an analytical result, which incorporates the calculated value, on a display device.

20 Claims, 5 Drawing Sheets

COMPUTER TOMOGRAPHY UNIT WITH A DATA RECORDING SYSTEM

This application is the national phase under 35 U.S.C. § 371 of PCT International Application No. PCT/DE03/01666 which has an International filing date of May 23, 2003, which designated the United States of America and which claims priority on German Patent Application number DE 102 25 613.6 filed Jun. 7, 2002, the entire contents of which are hereby incorporated herein by reference.

FIELD OF THE INVENTION

The invention generally relates to a computed tomography unit (CT unit) having a radiation receiver. Preferably the receiver has a number of detector elements, having a data acquisition system for reading the electrical signals which are produced by the detector elements and for processing them to form raw data, and having an image computer which is arranged downstream from the data acquisition system and to which the raw data can be supplied via a data transmission path.

BACKGROUND OF THE INVENTION

U.S. Pat. No. 6,264,365 B1 describes the monitoring of CT data, which is carried out in the background, with respect to the existence and localization of a defective radiation receiver.

SUMMARY OF THE INVENTION

An embodiment of the invention is based on an object of specifying a computed tomography unit in which the influence of changes such as aging, wear, dirt or other external disturbance influences on operation can be further reduced.

According to an embodiment of the invention, an object may be achieved by a computed tomography unit. The computed tomography unit includes an evaluation device which is designed for automatic assessment of the quality of the radiation detector and, in addition, for automatic assessment of the quality of the data acquisition system and/or of the data transmission path.

For the purposes of an embodiment of the invention, the expression raw data refers to any initial data from the DMS, irrespective of whether it has been produced with or without X-ray radiation arriving at the radiation receiver.

An embodiment of the invention is based, inter alia, on the discovery that all of the components of a data measurement system (DMS) for a CT unit, which includes the radiation receiver, the data acquisition system (DAS) and the data transmission path, are subject to undesirable changes which have a negative influence on the image quality. Such changes may result from aging, wear or dirt on the components themselves, or else from external disturbance influences—which possibly occur only over the course of time.

The computed tomography unit according to an embodiment of the invention, that is to say in which an evaluation device is integrated, has the advantage that, after a start event (which is produced, for example, by a person or by the computed tomography unit), the evaluation device operates automatically and without any further inputs (or at least without any further complex inputs) and thus allows a quality assessment to be carried out without a major time penalty. It is thus possible for a technician in the manufacturing phase, on the test panel or during a service visit to quickly make a statement on the current quality of the operation of the DAS or about the data transmission path, and to do this without having to connect an external test set for this purpose and having to link this by data connection to the CT unit. Once a statement about poor quality or a negative test result is available, the technician can if necessary carry out component replacements, readjustment of components and/or repair of components in the CT unit.

A further advantage is that, since there are no interactive actions, the probability of errors in carrying out the quality test is reduced, and the reproducibility of the test results is increased.

According to one preferred refinement, the following steps can be carried out by the evaluation device:
a) initiation of one or more measurements for production of raw data,
b) using the raw data, calculation of at least one value of at least one parameter which allows a quality statement,
c) driving of a display device (20) in order to display an evaluation result in which the calculated value is included.

The evaluation device preferably automatically initiates a change to the drive or setting of components in the CT appliance, in particular the X-ray beam source, the radiation receiver and/or the data acquisition system, while the measurement or measurements is or are being carried out, or between two measurements.

The advantages described above are obtained in particular if a number of parameters which indicate quality are displayed, in particular simultaneously, on the display device.

Since one or more predetermined parameters, that is to say parameters which are implemented in the evaluation device, are calculated using predetermined algorithms, that is to say a previously defined configuration process is carried out by the evaluation device or by its algorithms, and because the calculations are very largely carried out without any interaction with the user, the probability of errors in carrying out the quality test, and the reproducibility of the test results, are further improved, in terms of the latter also with respect to comparability of the test results which are obtained with different computer tomography units in one and the same series. The computed tomography units for this purpose are all equipped, for example, with the same evaluation device.

By way of example, the evaluation device first of all triggers the acquisition of raw data by measurements with or without X-ray radiation. The evaluation device can then determine the value of the parameter statistically from the measured raw data. Finally, the values of the parameter or parameters can be displayed.

It is advantageous for rapid acquisition of the quality state for the evaluation result to be displayed graphically on the display device, with the graphic including, in particular, a number of parameters relating to a graphical pattern, such as a bar chart, a column chart and/or a pie chart. A person carrying out the test can then see at a glance, and without having to record numerical values, whether or not the quality is "in the green band".

According to one development or alternative method of operation, tests which differ from one another can be carried out using configurations which differ from one another by way of different start events for the computed tomography unit according to an embodiment of the invention and, in particular, can also result in test patterns which differ from one another being displayed.

The alternatives, which include the determination of a number of parameters, can be illustrated as follows: let us assume that the linearity of a detector element and a quality value for the data transmission path have been predetermined as parameters. It is then possible to use a single start event to determine both the linearity parameter and the quality value, that is to say to obtain a comprehensive test result for a number of components in one procedure. Alternatively, start events which differ from one another can be used to carry out a test specifically on the detector element (linearity) or specifically on the data transmission path (quality value).

BRIEF DESCRIPTION OF THE DRAWINGS

One exemplary embodiment of a computed tomography unit according to the invention will be explained in more detail in the following text with reference to FIGS. 1 to 3, in which.

DETAILED DESCRIPTION OF THE EXEMPLARY EMBODIMENTS

Figure 1:
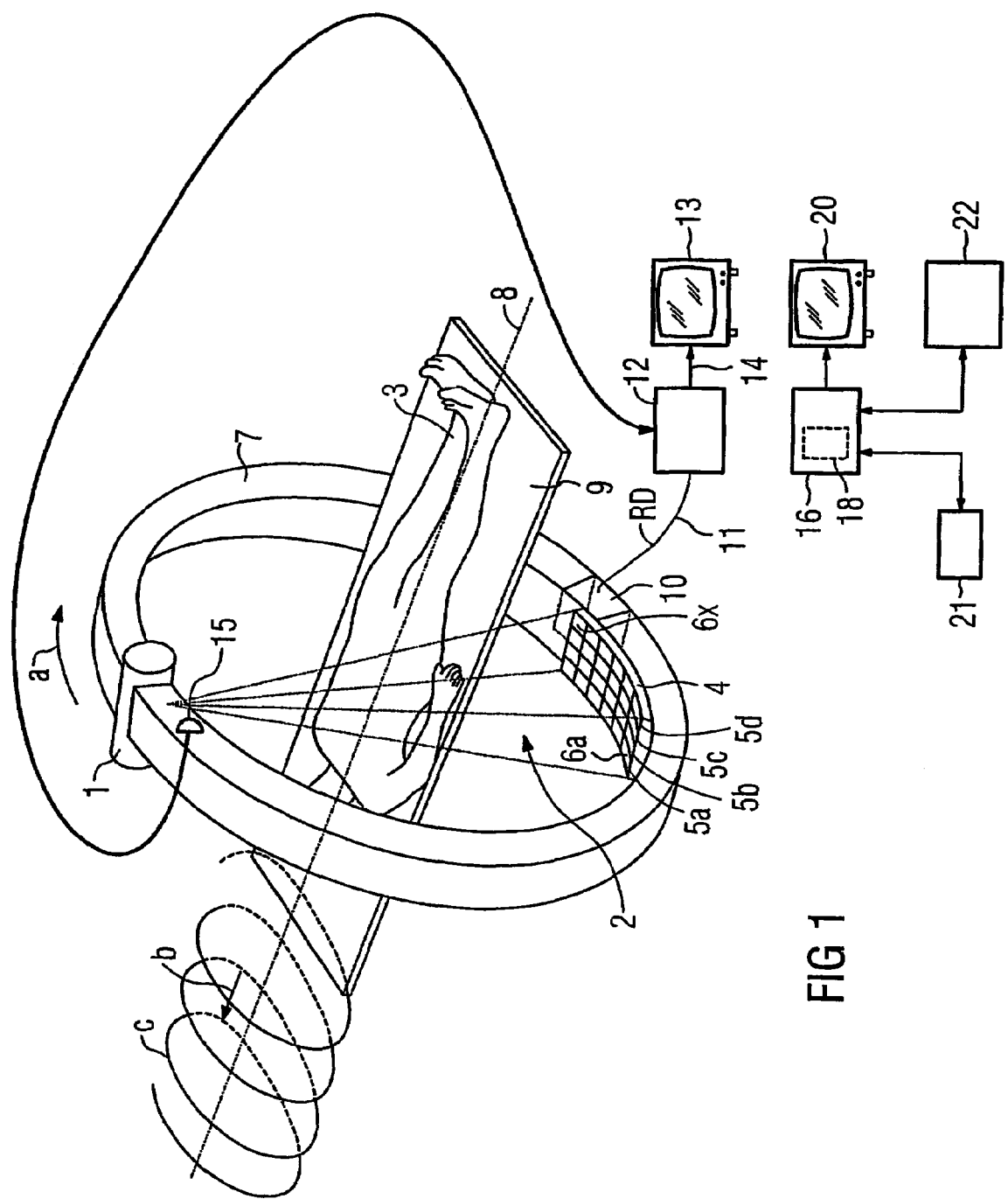
FIG. 1 shows a computed tomography unit according to an embodiment of the invention, in the form of a schematic overall view.

FIG. 1 shows, schematically, a computed tomography unit according to an embodiment of the invention with an X-ray beam source 1 which emits a pyramid-shaped X-ray beam 2, whose edge beams are illustrated by dashed-dotted lines in FIG. 1, which passes through an object being examined, for example a patient 3, and arrives at a radiation detector 4 which is equipped with a so-called UFC ceramic as a scintillator. The radiation detector 4 includes 4 or 16 detector rows 5a to 5d, which are arranged alongside one another and have a number (for example 672) of detector elements 6a to 6x arranged alongside one another.

The X-ray beam source 1 and the radiation detector 4 are arranged opposite one another on an annular scanning unit or gantry 7. The gantry 7 is mounted on a holding apparatus, which is not illustrated in FIG. 1, such that it can rotate with respect to a system axis 8 which runs through the center point of the annular gantry 7 (see the arrow a).

The patient 3 lies on a table 9 which is transparent for X-rays and which is mounted such that it can be moved along the system axis 8 by way of a mounting apparatus, which is likewise not illustrated in FIG. 1 (see the arrow b).

The X-ray source 1 and the radiation detector 4 thus form a measurement system which can be rotated relative to the system axis 8 and can be moved along the system axis 8 relative to the patient 3, so that the patient 3 can have radiation passed through him from different projection angles and in different positions with respect to the system axis 8. The output signals which are produced from the individual detector elements 6a to 6x in this case are read, conditioned and digitized by a data acquisition system 10, which is essentially arranged on the gantry 7. The digitized signals, the so-called raw data RD, are or is supplied by means of a transmission path 11, which contains an electrical cable and/or an optical waveguide as well as a slipring system or a wire-free transmission path (in a manner which is not illustrated), to a signal processing appliance or to an image computer 12, which calculates an image of the patient 3, and this image can in turn be reproduced on a monitor 13. The monitor 13 is connected to the image computer 12 by means of an electrical cable 14. The steps of air calibration, channel correction for non-linearities, spacing correction, water calibration and image reconstruction, inter alia, are carried out in the image computer 12.

The data acquisition system 10 contains a radiation monitor 15 which is arranged on the emitter side, measures the radiation power of the X-ray beam source 1, and whose output signal is used in the image computer 12 for normalization of the raw data. The entire signal channel which is associated with the radiation monitor 15 is also referred to as the monitor channel.

The computed tomography unit illustrated in FIG. 1 can be used both for sequence scanning and for spiral scanning.

In the case of sequence scanning, the patient 3 is scanned in layers. In this case, the X-ray beam source 1 and the radiation detector 4 are rotated around the patient 3 with respect to the system axis 8, and the measurement system, which includes the X-ray beam source 1 and the radiation detector 4, in each case records an attenuation profile (linear integral) in each of a large number of projections, in order to scan a two-dimensional layer of the patient 3. The image computer 12 uses the measured values (raw data RD) obtained in this way to reconstruct a section image which represents the scanned layer. The patient 3 is in each case moved along the system axis 8 between the scanning of successive layers. This procedure is repeated until all of the layers of interest have been recorded.

During spiral scanning, the measurement system, which includes the X-ray beam source 1 and the radiation detector 4, is rotated with respect to the system axis 8. Further, the table 9 is moved continuously in the direction of the arrow b, that is to say the measurement system which includes the X-ray beam source 1 and the radiation detector 4 is moved relative to the patient 3 continuously on a spiral path c until the area of the patient 3 of interest has been recorded completely. A volume data record is generated in this case. The image computer 12 uses this to calculate planar data, using an interpolation process, from which section images are reconstructed, in the same way as for sequence scanning.

An evaluation device 18 is provided in a control computer (host) or computer 16 which is fitted away from the gantry 7, that is to say it is stationary, and is formed as a functional group by driving the computer 16 via software provided in the computer 16. The evaluation device 18 is used for automated assessment of the quality of the DMS (Data Measuring System), which comprises the data acquisition system 10, the transmission path 11 and the radiation detector 4. Evaluation algorithms are run in the computer 16 for this purpose.

Once the evaluation device 18 has been triggered, it carries out the following steps automatically, without any further human inputs being required:

a) initiation of one or more measurements for production of raw data, which is also supplied to the computer 16 via the data transmission path 11;

b) using the direct raw data or raw data which has been normalized on the basis of the monitor channel, calculation of at least one value of at least one parameter which allows a quality statement;

c) driving of a display device 20 in order to display an evaluation result, in which the calculated value is included.

Depending on the respective specific parameter calculation, after step b) the evaluation device 18 carries out a comparison of the calculated value with a tolerance limit which can be predetermined or is read from a memory 21. A comparative illustration can then be displayed in the evaluation result on the display device 20.

The evaluation result is displayed graphically.

To allow comparison with earlier quality tests, in particular for assessment of the long-term stability of the data acquisition system 10 and of the radiation detector 4, evaluation results can be stored in a memory device 22, and can be reloaded from there, in particular for a parameter which results from a comparative calculation.

The exemplary embodiments which are described in the following text describe in detail the method of operation, as demonstrated with reference to FIG. 1, of the evaluation device 18 for specific test measurements.

Figure 2:
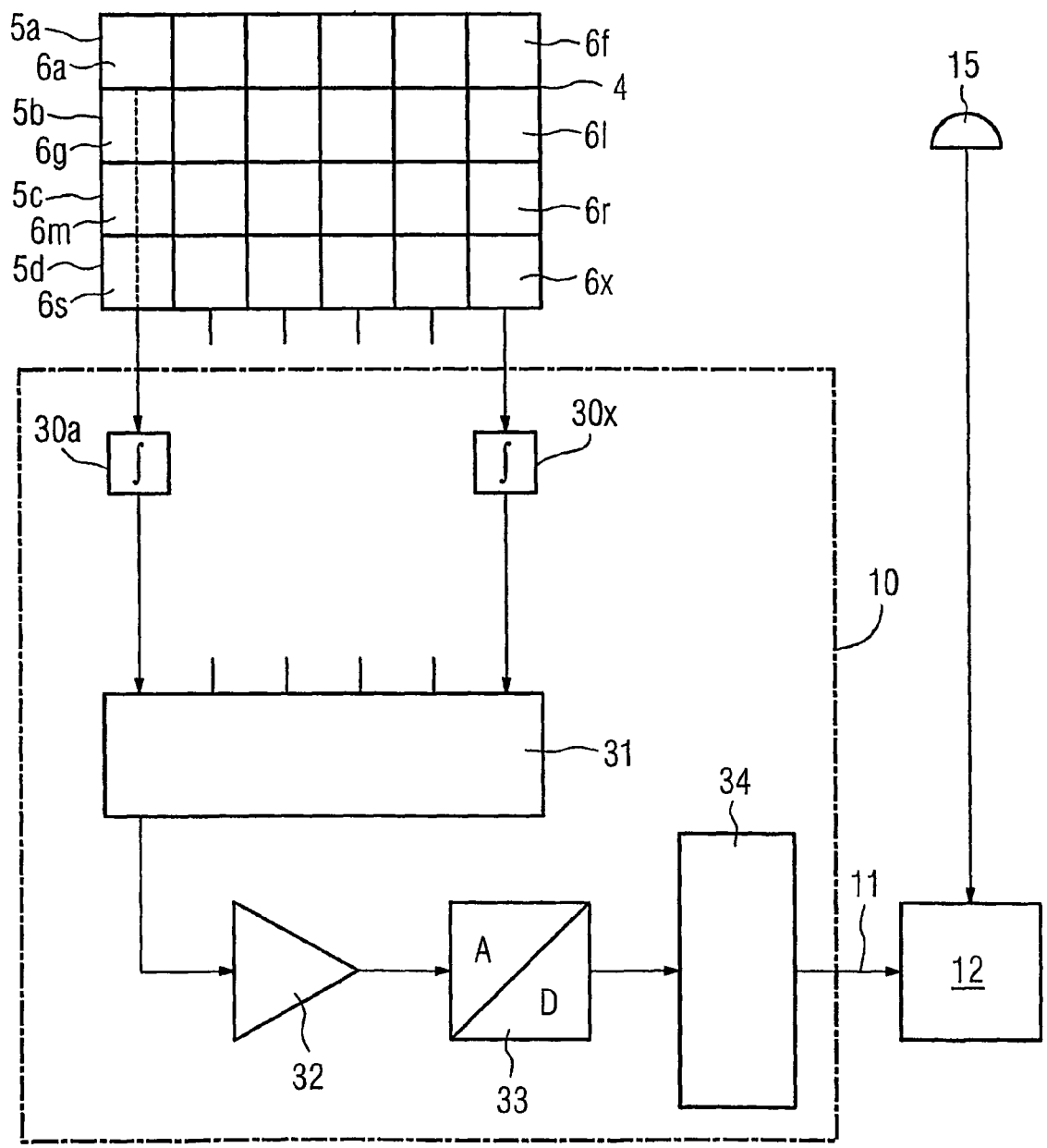
FIG. 2 shows a data acquisition system for the computed tomography unit shown in FIG. 1.

FIG. 2 shows, schematically and in detail, the data acquisition system 10 as illustrated in FIG. 1, whose function and quality are tested by the evaluation device 18.

Each detector element 6a to 6x is followed by a respective integrator 30a to 30x, which is a capacitor. FIG. 2 illustrates only the integrators 30a and 30x. The integrators 30a to 30x may also, in contrast to FIG. 2, be formed by amplifier stages or, to the extent that they are a component of the detector elements 6a to 6x, may themselves have an integrating effect as the detector elements 6a to 6x.

The integrators 30a to 30x integrate the charges (which are produced in the detector elements 6a to 6x on absorption of X-ray radiation) for each sampling step over a specific time interval, and these charges are read and amplified row-by-row sequentially by means of a demultiplexer 31 and by way of an electronics element 32. That is to say, the signals which have been read are applied sequentially at the output of the electronics element 32 firstly to the detector element 6a, then to the detector elements 6b to 6f, and then to the detector elements 6g to 61, and so on. Alternatively, the detector elements 6a to 6x may also be read in columns.

The signals from the detector elements 6a to 6x, after having been read and amplified by means of the electronics element 32, are then digitized sequentially by way of an analog/digital converter 33, and are optionally supplied to a so-called arithmetic logic unit (ALU) 34. The digitized signals are supplied to the image computer 12 via the transmission path.

In order to test individual components of the data acquisition system 10, the evaluation device 18 carries out a number of measurements successively, on the basis of which it is possible to assess whether and if appropriate where in the signal path a quality defect has occurred in the data acquisition system 10, so that any fault or defect which may be present can be associated, at least with a high probability, with a specific component.

The evaluation device 18 offers various algorithms for testing of the radiation detector 4 and of its detector elements 6a–6x, with the particularly advantageous evaluations being described in the following text:

A) Check of the Offset Values (Signal Offset) of the Detector Elements 6a–6x:

The offset values are dark values (without X-ray radiation), which are preset in order to allow correct A/D conversion. The offset values must be in a specific optimum range. This check may also be regarded as a check of the "detector channels".

After it has been triggered, the evaluation device 18 carries out the following steps automatically:

a) Initiation of the recording of a raw data record with the gantry 7 revolving or being stationary, but with the X-ray beam source 1 switched off. 1000 to 2000 individual values are typically recorded in this case for each detector element 6a–6x.

b) A mean value and a standard deviation are calculated from the individual values for each detector channel as parameters which allow a quality statement.

c) The means values and standard deviations are displayed as numerical values or as a bar chart (for example with a channel number on one of the diagram axes) on the display device 20.

Figure 3:
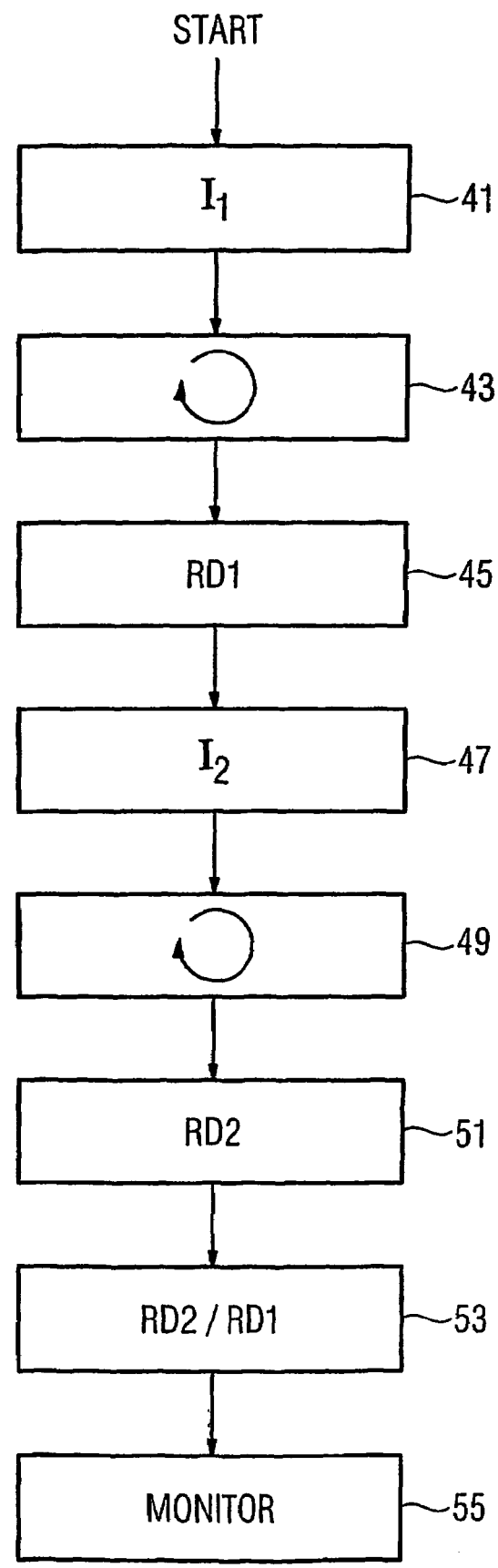
FIG. 3 shows a flowchart relating to the checking of the signal linearity of the detector channels.

B) Check of the Signal Linearity (Relationship Between the Received Signal and the Incident X-ray Radiation Power) FIG. 3 shows a corresponding flowchart.

After the start, the evaluation device 18 first of all, in a first step 41, sets the X-ray beam source 1 with a first tube current $I_1$. In a second step 43, the gantry 7 is revolved, and data from the detector elements 6a–6x is measured. During the process, a first raw data record RD1 is formed successively or subsequently in a third step 45. In a fourth step 47, a second tube current $I_2$ is set, which is not the same as the first, and another gantry revolution is carried out in a fifth step 49, with a second raw data record RD2 being formed in a sixth step 51. The tube voltage and thus the X-ray spectrum remain the same for both raw data records RD1, RD2. The raw data records RD1, RD2 are used to form ratios on a channel basis in a seventh step 53, and are related to the ratio of the tube currents $I_1$, $I_2$. A test result which includes both ratios is either displayed immediately for each channel, or first of all only for each row, with the option of obtaining a recording of the test results from the individual channels only if the test result is unsatisfactory (eighth step 55).

C) Check of the spectral linearity (relationship between the received signal and the spectral composition of the incident X-ray radiation)

Figure 4:
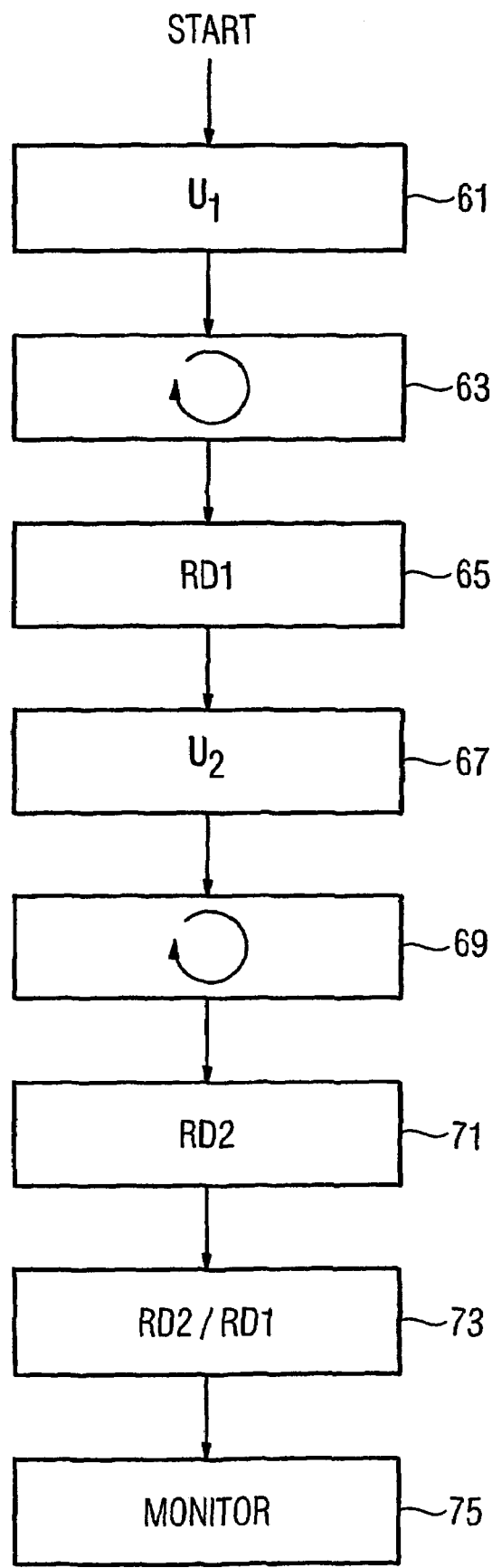
FIG. 4 shows a flowchart relating to the checking of the spectral linearity of the detector channels.

FIG. 4 illustrates a corresponding flowchart.

After the start, the evaluation device 18 first of all sets the X-ray beam source 1 to a first tube voltage $U_1$ in a first step 61. In a second step 63, one revolution of the gantry 7 is carried out, and data is measured from the detector elements 6a–6x. During this process, a first raw data record RD1 is formed successively or subsequently in a third step 65. A second tube voltage $U_2$, which is not the same as the first, is set in a fourth step 67, another gantry revolution is carried out in a fifth step 69, and a second raw data record RD2 is formed in a sixth step 71. The tube power remains the same for both raw data records RD1, RD2, that is to say the tube current has been matched appropriately. The ratios of the two raw data records RD1, RD2 are formed on a channel basis in a seventh step 73, and are related to the ratio of the tube voltages $U_1$, $U_2$. A test result which includes both ratios is either displayed immediately for each channel, or first of all only for each row, with the option of obtaining a recording of the test results of the individual channels only if the test result is unsatisfactory (eighth step 75).

Figure 5:
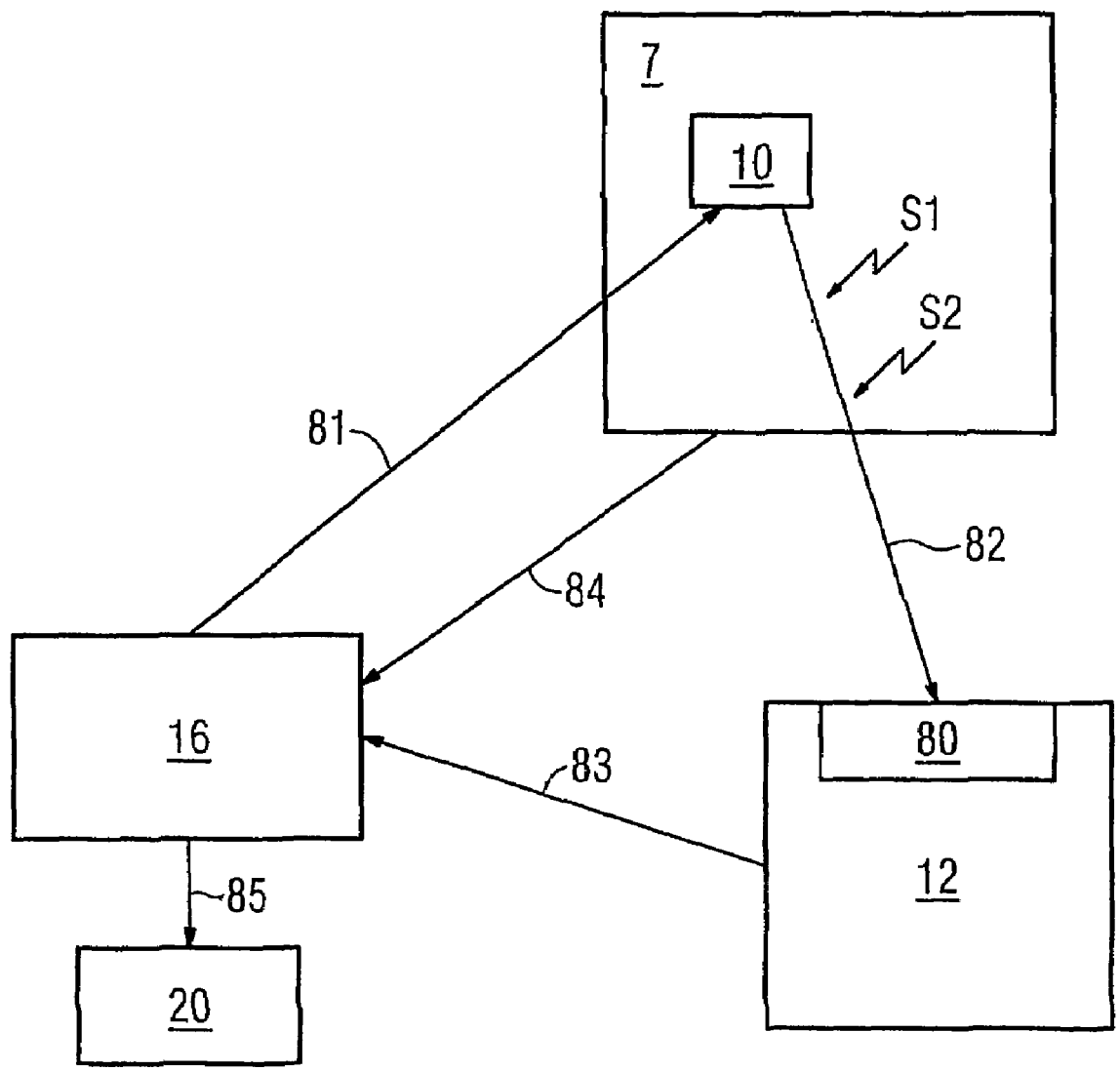
FIG. 5 shows a schematic illustration of the checking of a data transmission path.

In order to test or check the data transmission path 11 from the radiation detector 4 to the image computer 12, the evaluation device 18, in this case in particular DMS test software in the monitoring computer 16 of the CT unit, drives the CT unit with or without X-ray radiation. This procedure is illustrated in FIG. 5.

First of all, the scan parameters required for the test are set (arrow 81). The data acquisition system 10 of the DMS is configured, for example by way of specific test settings on microcontrollers, so as to produce predefined test data. A number of scans (measurements) are then carried out.

The data produced by the data acquisition system 10 is transmitted via optical waveguides and a slipring to the receiver 80 for the image computer 12 (arrow 82). The signal may be subject to disturbances on the transmission path 11, for example by the production of the X-ray radiation (interference S1) and by the ring motor of the gantry drive (interference S2). In order to make it possible to distinguish between the different interference sources, separate tests are carried out:

i) scans with radiation and without radiation in order to identify faults which are caused by the production of the X-ray radiation,
ii) scans without radiation and with rotation in order to identify faults which are caused by the drive.

The image computer 12 then carries out consistency tests on the received data, for example by forming bit cross sums by means of CRC (Cyclic Redundancy Check), by analyzing the amount of received data, and/or by analyzing the values of the received data.

The test software in the host computer 16 checks the faults which occur during the measurements from the image computer 12 (arrow 83) and from slipring electronics (arrow 84) and produces these faults in the form of texts and graphics. The results are displayed on the display device 20 (arrow 85).

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A computer tomography unit, comprising:
an X-ray beam source;
a radiation detector including a plurality of detector elements;
a data acquisition system for reading the electrical signals produced by the detector elements and for processing the signals to form raw data;
an image computer, arranged downstream from the data acquisition system, for receiving the raw data via a data transmission path; and
an evaluation device, designed for automatic assessment of the quality of the radiation detector and for automated assessment of the quality of the data acquisition system and the data transmission path, wherein the evaluation device is adapted to perform the following,
initiating at least one measurement for production of dark value data with the X-ray beam source switched off,
calculating, using the dark value data, at least one value of a parameter describing a signal offset of the radiation detector and a further parameter for assessment of the data transmission path, and
driving a display device to display an evaluation result including the calculated value.

2. A computer tomography unit of claim 1, wherein,
the evaluation device is adapted to initiate at least two measurements for production of raw data, at least one measurement producing dark value data, and wherein at least one of the drive and setting of the X-ray beam source is automatically changed between the at least two measurements.

3. The computer tomography unit as claimed in claim 2, wherein the parameter describes at least one of spectral linearity and signal linearity of the radiation detector.

4. The computer tomography unit as claimed in claim 2, wherein the evaluation device is adapted to compare the calculated value with a tolerance limit which is at least one of predetermined and read from a memory.

5. The computer tomography unit as claimed in claim 2, wherein the evaluation result is displayable graphically on the display device.

6. The computer tomography unit as claimed in claim 4, wherein two or more parameters are combined to form a graphical pattern.

7. The computer tomography unit as claimed in claim 2, further comprising a memory device for storage of the evaluation result.

8. The computer tomography unit as claimed in claim 2, wherein a further parameter is determinable which is suitable for assessment of the quality of at least one of the data acquisition system, a component of, a module element of and a subarea of the data acquisition system.

9. The computer tomography unit as claimed in claim 8, wherein the parameter is suitable for at least one of assessment of an integrator in the electronics channel, assessment of a monitor channel, assessment of a demultiplexer, and assessment of an A/D converter.

10. The computer tomography unit as claimed in claim 2, wherein the evaluation device determines the value of the parameter statistically from the measured dark value data.

11. The computer tomography unit as claimed m claim 2, wherein the evaluation device is implemented by use of appropriate software which is provided in a control computer fitted away from a gantry.

12. The computer tomography unit as claimed in claim 1, wherein the evaluation device is adapted to compare the calculated value with a tolerance limit which is at least one of predetermined and read from a memory.

13. The computer tomography unit as claimed in claim 1, wherein the evaluation result is displayable graphically on the display device.

14. The computer tomography unit as claimed in claim 13, wherein two or more parameters are combined to form a graphical pattern.

15. The computer tomography unit as claimed in claim 1, further comprising a memory device for storage of the evaluation result.

16. The computer tomography unit as claimed in claim 1, wherein a parameter is determinable which is suitable for assessment of the quality of at least one of the data acquisition system, of a component of, a module element of and a subarea of the data acquisition system.

17. The computer tomography unit as claimed in claim 16, wherein the parameter is suitable for at least one of assessment of an integrator in the electronics channel, assessment of a monitor channel, assessment of a demultiplexer, and assessment of an A/D converter.

18. The computer tomography unit as claimed in claim 16, wherein the evaluation device determines the value of the parameter statistically from the measured dark value data.

19. The computer tomography unit as claimed in claim 1, wherein the evaluation device is implemented by use of appropriate software which is provided in a control computer fitted away from a gantry.

20. The computer tomography unit as claimed in claim 1, wherein the evaluation device determines the value of the parameter statistically from the measured dark value data.

* * * * *